(12) United States Patent
Bates

(10) Patent No.: US 8,603,512 B2
(45) Date of Patent: Dec. 10, 2013

(54) METHODS FOR TREATING AN INJURED NERVE PATHWAY

(75) Inventor: Mark C. Bates, Charleston, WV (US)

(73) Assignee: Nexeon Medsystems, Inc., Charleston, WV (US)

( * ) Notice: Subject to any disclaimer, the term of this patent is extended or adjusted under 35 U.S.C. 154(b) by 433 days.

(21) Appl. No.: 12/950,769

(22) Filed: Nov. 19, 2010

(65) Prior Publication Data

US 2011/0066169 A1    Mar. 17, 2011

Related U.S. Application Data

(62) Division of application No. 10/977,593, filed on Oct. 29, 2004, now Pat. No. 7,842,304.

(51) Int. Cl.
| A61B 17/08 | (2006.01) |
| A61F 2/00 | (2006.01) |
| A61K 48/00 | (2006.01) |
| A61M 31/00 | (2006.01) |

(52) U.S. Cl.
USPC .......... 424/423; 424/93.21; 604/57; 604/506; 606/152

(58) Field of Classification Search
USPC ........... 424/423, 93.21; 604/57, 506; 606/152
See application file for complete search history.

(56) References Cited

U.S. PATENT DOCUMENTS

| 5,607,477 | A | 3/1997 | Schindler et al. |
| 6,551,275 | B2 | 4/2003 | Fontayne et al. |
| 6,939,318 | B2 | 9/2005 | Stenzel |
| 7,001,410 | B2 | 2/2006 | Fisher et al. |
| 2002/0137706 | A1 | 9/2002 | Evans et al. |
| 2004/0156878 | A1 | 8/2004 | Rezania et al. |
| 2004/0210209 | A1 | 10/2004 | Yeung et al. |
| 2005/0032209 | A1 | 2/2005 | Messina et al. |

OTHER PUBLICATIONS

Benes et al. Experimental spinal cord injury: lumbar vertebra resection to shorten the gap between spinal cord stumps. Acta Neurochir (Wien). 1988;90(3-4):152-6 (Abstract only; p. 1).*
Gruh et al. 2009. Transdifferentiation of Stem Cells: A Critical View. Adv Biochem Engin/Biotechnol. 114: 73-106.
Watson et al. 1994. An electrophysiological and histological study of trypsin induced demyelination. JNeurol Sci. 126(2): 116-25 (abstract only: p. 1-2).
Meriam-Webster Online Dictionary. 2010. Definition for "anchor" http://www.merriam-webster.comldictionary/anchor. p. 1.
Cell Dissociation. 2010. Sigma-Aldrich. http://www.sigmaaldrich.cornllife-science/metabolomics/enzyme-explorer/analytical-enzymes/trypsin/cell-dissociation.html. p. 1.
Meriam-Webster Online Dictionary. 2010. Definition for "grid" http://www.merriam-webster.comldictionary/grid. p. 1.
International Search Report for PCT/US2005/038876, 3 pages (mailed Nov. 2, 2007).
Written Opinion of the International Searching Authority for PCT/US2005/038876, 6 pages (mailed Nov. 2, 2007).
Watson et al., "An electrophysiological and histological study of trypsin induced demyelination," J. Neurosci. Res. 126(2):116-125 (1994).

* cited by examiner

*Primary Examiner* — Taeyoon Kim
(74) *Attorney, Agent, or Firm* — Foley & Lardner LLP; Nicola A. Pisano; Christopher C. Bolten

(57) ABSTRACT

Methods and apparatus are provided for treating an injured or severed nerve pathway, wherein one or more microporous tubes are implanted into the nerve pathway to bridge the injured or severed region. A bioactive matrix including stem cells and nutrients is disposed within the microporous tube to facilitate growth of the stem cells and reestablishment of the sensory and motor conductive pathways through the injured or severed region. The microporous tube protects the bioactive matrix during development of the stem cells, and also retains the end regions in proper alignment during the nerve pathway regeneration.

4 Claims, 3 Drawing Sheets

METHODS FOR TREATING AN INJURED NERVE PATHWAY

CROSS-REFERENCE TO RELATED APPLICATIONS

This application is a divisional of U.S. patent application Ser. No. 10/977,593, filed Oct. 29, 2004, now U.S. Pat. No. 7,842,304, the entire contents of which are incorporated herein by reference.

FIELD OF THE INVENTION

The present invention relates to apparatus and methods for treating an injured nerve pathway, such as the spinal cord.

BACKGROUND OF THE INVENTION

Spinal cord injuries may arise from car accidents, violent crimes, falls and sports injuries. Spinal cord injury is a major neurological problem since most damage resulting from the injury is irreversible. Injured nerves fibers do not normally regenerate with resulting loss of nerve cell communication, leading to paralysis and loss of sensation.

After spinal cord severance, a new glial basal lamina forms to cover the exposed surface of the cord end regions. The glial cells also secrete barrier molecules that are difficult to penetrate, further suppressing reestablishment of nerve interconnections. The spinal cord tissue bordering the severed region becomes necrotic, detaches from the spinal cord, and develops irregular cavities.

Most tissue in the human body originates from undifferentiated cells known as stem cells. These fundamental building blocks differentiate into specific target parenchymal tissue based on hormonal signals. Scientific evidence suggests that stems cells injected into a target tissue will differentiate into a cell line specific to the host tissue. This capability is of particular interest in treating conditions involving organs, such as the spinal cord, that cannot regenerate.

Initial enthusiasm concerning stem cell implantation in patients was tempered by the ethical and logistic concerns of utilizing embryonic stem cells. Recent developments in stem cell research suggest adult stem cells can be harvested from the bone marrow and other tissues. Many such "cell lines" have been generated and are undergoing clinical evaluation. If successful, this work will obviate the moral and ethical dilemma of utilizing tissue from embryos for research.

While it has been suggested that stem cells could be used to repair spinal cord injury, there currently is no method or apparatus available to promote reestablishment of nerve pathways through the glial basal lamina or necrotic regions that develop at the injury situs. Accordingly, the suggestions in the prior art to use stem cells to regenerate damaged regions of the spinal cord remain more fantastic than practical. In addition, efforts to directly inject stem cells into an injured spinal cord region could both injure the cell membranes and disrupt the delicate intercellular matrix, thereby causing further injury to the target tissue.

In view of the foregoing, it would be desirable to provide methods and apparatus for treating severed or injured nerve pathways by delivering a bioactive matrix, e.g., stem cells, within or adjacent to an injured nerve pathway so as to span or bridge injured or necrotic portions. In this manner, the bioactive matrix may promote nerve regeneration to restore conductive pathways across the injured region.

It would be also desirable to provide methods and apparatus for treating nerve pathway injury by delivering a bioactive matrix so as to reduce the risk of injury to stem cells within the bioactive matrix or to the target tissue.

It would be further desirable to provide apparatus and methods for treating nerve pathway injury by delivering a bioactive matrix to damaged tissue to promote tissue regeneration, wherein the apparatus and methods reduce physical trauma to the bioactive matrix during delivery, and enhance the proportion of viable material delivered to the damaged tissue.

It further would be desirable to provide apparatus and methods for treating a nerve pathway injury that promotes regeneration of both sensory and motor nerves.

SUMMARY OF THE INVENTION

In view of the foregoing, it is an object of the present invention to provide methods and apparatus for treating nerve pathway injury by delivering a bioactive matrix, e.g., stem cells, within or adjacent to an injured nerve pathway so as to span or bridge injured or necrotic portions. In this manner, the bioactive matrix may promote nerve regeneration to restore conductive pathways across the injured region.

It is another object of this invention to provide methods and apparatus for treating nerve pathway injury by delivering a bioactive matrix so as to reduce the risk of injury to stem cells within the bioactive matrix or to the target tissue.

It also is an object of this invention to provide apparatus and methods for treating nerve pathway injury by delivering a bioactive matrix to damaged tissue to promote tissue regeneration, wherein the apparatus and methods reduce physical trauma to the bioactive matrix during delivery, and enhance the proportion of viable material delivered to the damaged tissue.

It is a further object of the present invention to provide apparatus and methods for treating nerve pathway injury that promotes regeneration of both sensory and motor nerves.

These and other objects of the present invention are accomplished by providing methods and apparatus for delivering a bioactive matrix, preferably that includes stem cells, into regions of an injured nerve pathway so that the bioactive matrix spans or bridges the injured or necrotic region. In accordance with the principles of the present invention, microporous tubes are first implanted within or across an injured or necrotic portion of nerve pathway so as to penetrate the glial basal lamina and bridge the damaged portions. A bioactive matrix, preferably including stem cells and essential nutrients to promote development of the stem cells, then is delivered into the microporous tubes. The stem cells develop within the microporous tubes and penetrate through the pores to interconnect with the surrounding nerve tissue, thereby promoting regeneration of both motor and sensory nerves.

The microporous tubes of the present invention fulfill a number of functions, including protecting the stem cells from mechanical injury, retaining the nutrient matrix that promotes growth of the stem cells, and providing a pathway and mechanical scaffold along which the nerves may regenerate. The pores of the tubes preferably are selected to permit the stem cells to penetrate the tube walls and establish interconnections with the surrounding nerve tissue. In addition, the microporous tubes may be employed to impart mechanical integrity to the injured region of the nerve pathway and retain severed portions in proper alignment. The microporous tubes may be constructed entirely of bioabsorbable material or alternatively may include non-biodegradable polymeric components. A coating containing antibodies to offset inhibitory influences and/or growth factors may be applied to the tubes to promote regeneration of surrounding tissue.

In a method of employing the above-described apparatus, a vertebral resection is performed to align severed portions of a spinal cord in apposition. One or more microporous tubes then are inserted into the spinal cord at predetermined locations so as to bridge the severed ends of the cord. A bioactive matrix then is delivered within the one or more microporous tubes. According to some embodiments, a grid may be employed to position the tubes across the severed portions of the spinal cord.

In an alternative embodiment of the present invention, the microporous tubes may be pre-loaded with a selected bioactive matrix to form rods or capsules. In this case, the needle may be used to form one or more passageways that span the injured portions of the nerve pathway. The pre-loaded microporous tubes then are inserted into the passageways where they are bioabsorbed, thereby releasing the bioactive matrix to promote nerve regeneration.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
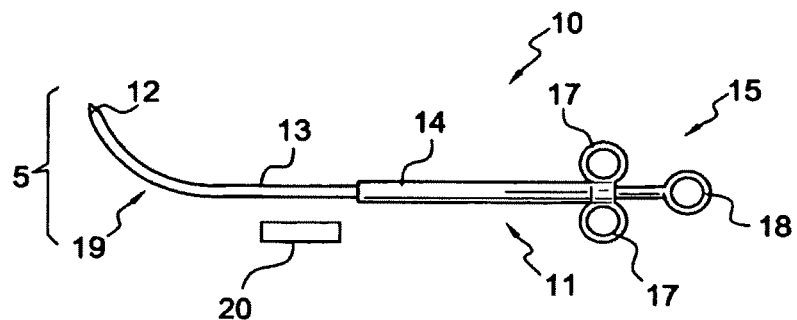
FIG. 1 is a plan view of an exemplary embodiment of the apparatus of the present invention.
Figure 2:
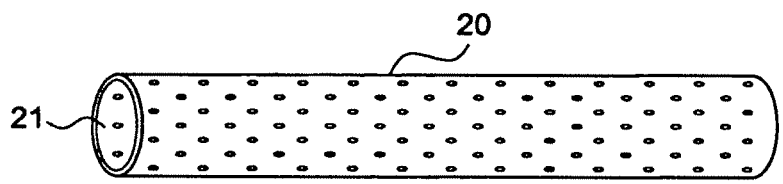
FIG. 2 is an enlarged perspective view of the microporous tube of FIG. 1.
Figure 3:
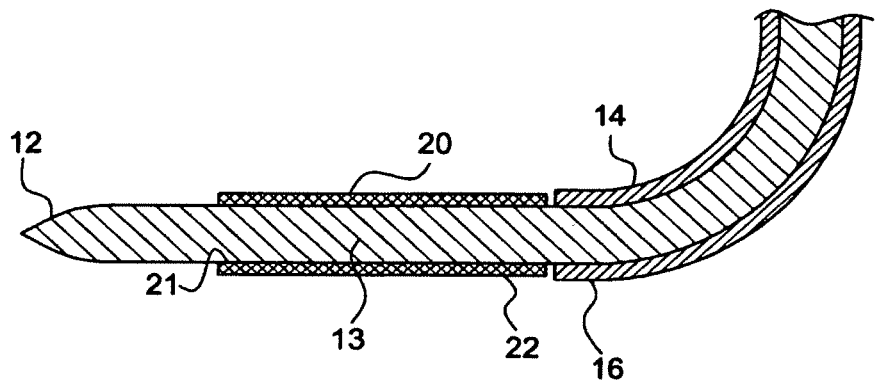
FIG. 3 is a side sectional view of the microporous tube of the present invention disposed on an insertion needle.

Referring to FIGS. 1-3, apparatus constructed in accordance with the principles of the present invention for treating an injured nerve pathway, such as the spinal cord, is described. Apparatus 5 comprises insertion device 10 and microporous tube 20. A bioactive matrix, preferably including stem cells and essential nutrients to promote development of the stem cells, is deposited within the microporous tubes to promote regeneration of nerve tissue that spans the injured or severed portion of the spinal cord.

Insertion device 10 comprises needle 11, which is illustratively curved and includes distal tissue-piercing tip 12, shaft 13, sheath 14 and handle 15. Microporous tube 20 includes lumen 21 having a diameter slightly larger than shaft 13 of needle 11, so that tube 20 may be slidably advanced over tip 12 and onto shaft 13. When disposed on shaft 13, the proximal end 22 of the tube abuts against the distal end 16 of sheath 14. Sheath 14 is slidably disposed on shaft 13. This arrangement permits microporous tube 12 to be ejected from shaft 13 by holding sheath 14 stationary using finger loops 17 and proximally retracting shaft 13 using finger loop 18. After the microporous tube is ejected from shaft 13 of needle 11, a conventional syringe may be used to deposit a bioactive matrix within lumen 21 of the tube.

Insertion device 10 preferably includes curved distal portion 19 of needle 11 that permits the needle to be inserted at an angle into a patient's spinal cord so that microporous tube 20 may be substantially aligned with the longitudinal axis of the spinal cord. Needle 11 may comprise a shape-memory metal alloy to retain a predetermined curvature in distal portion 19, or may comprise a suitable stainless steel alloy. Shaft 13 preferably comprises a radiopaque material to facilitate the positioning of the microporous tube under fluoroscopic guidance. Sheath 14 preferably comprises a flexible polymer, e.g. polyethylene, of sufficient thickness to provide an abutment surface for the proximal end of the microporous tube during insertion of needle 11 and tube 20 into the spinal tissue, and during subsequent retraction of shaft 13.

Microporous tube 20 preferably comprises a material having through-wall pores with an effective diameter in a range of 50 to 200 microns. As will of course be understood, the pores need not be circular in shape, but may be irregular and of various sizes. As would be understood to those of ordinary skill in the art, microporous tube 20 may comprise various shapes (other than substantially cylindrical) without departing from the scope of the present invention.

The microporous tube of the present invention may be made by casting a suitable bioabsorbable material in a tubular shape, and then using a laser to create the through-wall holes. Alternatively, tube 20 may be constructed by depositing spun fibers on a rotating spindle, as is known in the art for the manufacture of polyester graft materials. Microporous tube 20 may in addition include non-absorbable polymeric fibers disposed with in the wall of the tube to provide additional mechanical strength and flexibility to the tube.

Microporous tube 20 preferably comprises a bioabsorbable material and retains damaged portions of the spine in correct alignment during tissue regeneration. One suitable material is poly lactic-co-glycolic acid ("PLGA"), which provides sufficient flexibility as well as the requisite strength to retain correct spinal alignment. Microporous tube 20 also may be coated on its interior surface, exterior surface, of both, with anti-rejection drugs and/or agents to promote regeneration of surrounding nerve tissue.

Figure 4:
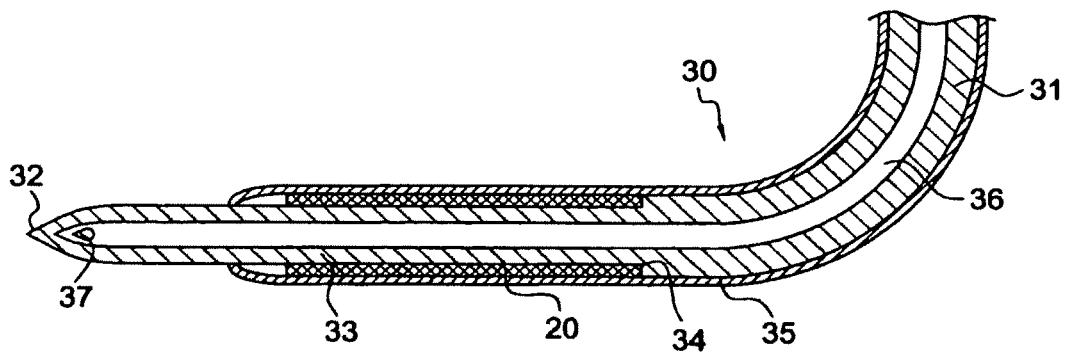
FIG. 4 is a side sectional view of an alternative apparatus for delivering a microporous tube and then depositing a selected bioactive matrix within the tube.

Referring now to FIG. 4, an alternative embodiment of the insertion device of the present invention is described. Insertion device 30 comprises needle 31 having tissue-piercing tip 32, reduced diameter region 33 that forms step 34, sheath 35, and lumen 36 that includes port 37. Microporous tube 20 is disposed on reduced diameter region 33 so that its proximal end abuts against step 34. Unlike the embodiment of FIGS. 1-3, wherein sheath 14 is used to eject microporous tube 20 at the target site, sheath 35 instead encloses the tube during delivery. Once needle 31 has been advanced to a target location with in the spinal cord, sheath 35 is retracted so that the microporous tube engages the surrounding nerve tissue. Needle 31 then is retracted to deposit microporous tube 20 in the needle track.

Lumen 36 is coupled to a source of bioactive matrix that is to be deposited in microporous tube 20 via port 37. Accordingly, during withdrawal of needle 31, the bioactive matrix may be delivered into lumen 21 of the microporous tube by low-pressure injection through lumen 36 and port 37 of needle 31. In this manner, an additional step of delivering the bioactive matrix into the microporous tube using, for example, a conventional syringe may be omitted.

Figure 5A:
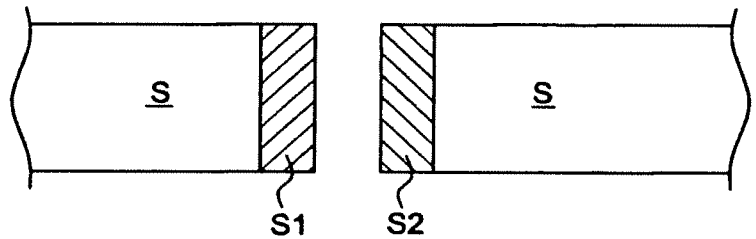
FIGS. 5A-5E are side sectional views illustrating a method of using the apparatus of the present invention.
Figure 5B:
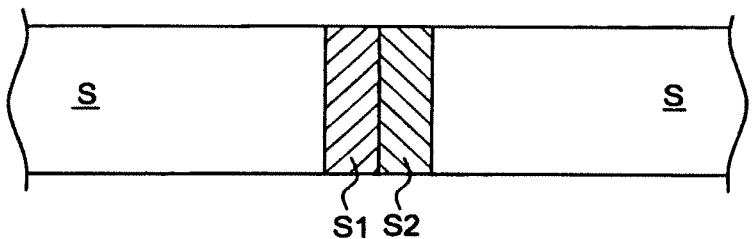

Referring now to FIGS. 5A-5E, methods of using the apparatus of FIG. 4 in accordance with the principles of the present invention are described. In FIG. 5A, severed spinal cord S includes end regions S1, S2 that have developed glial basal laminae, scar tissue and areas of cavitation and necrosis. Illustratively, a space exists between the end regions due to cell retraction. Accordingly, an initial step of the method of the present invention may involve aligning end regions S1, S2 using vertebral resection to move the end regions into apposition and eliminate the space therebetween, as depicted in FIG. 5B.

Figure 5C:
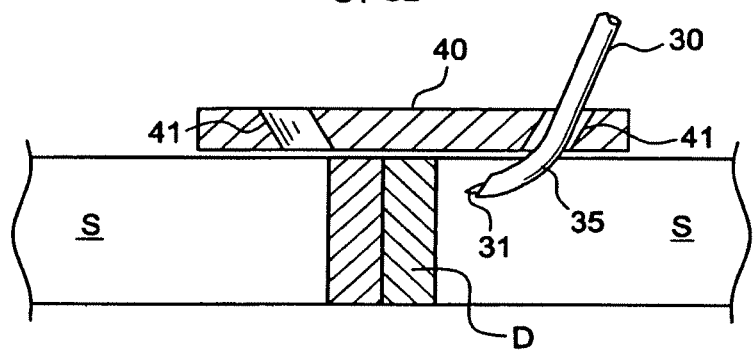

In FIG. 5C, grid 40 may be positioned along spinal cord S relative to the end regions so that the longitudinal axis of the grid is substantially parallel to spinal cord S. Grid 40 includes a plurality of apertures 41 disposed at predetermined locations and angles that guide insertion device 40 into spinal cord S in a predetermined pattern. Needle 31 and microporous tube 20 are advanced through end regions S1 and S2 so that the microporous tube is disposed substantially parallel to spinal cord S. Grid 40 also lends structural support to spinal cord S during the procedure.

Figure 5D:
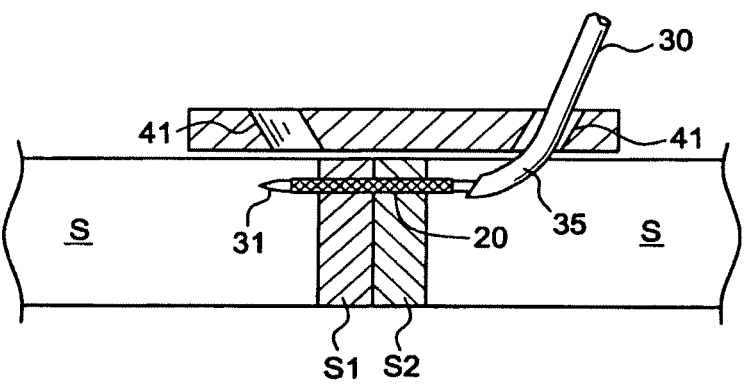
Figure 5E:
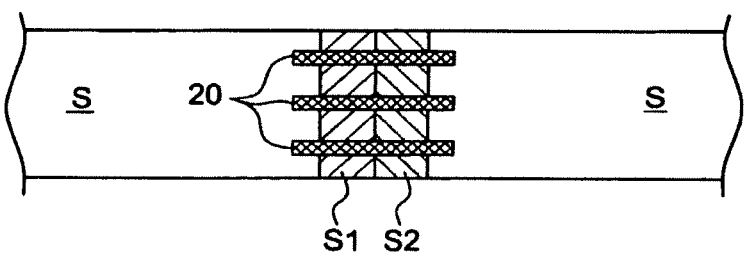

In FIG. 5D, sheath 35 is retracted proximally to deposit microporous tube 20 in the needle track, and needle 31 then is withdrawn from lumen 21 of microporous tube 20, leaving the tube spanning end regions S1, S2. A bioactive matrix of stem cells and culture medium may then be deposited within the microporous tube using a conventional needle. Care should be exercised during deposition of the bioactive matrix so as to reduce trauma to the bioactive matrix during delivery. The above-described process is repeated using different apertures 41 of grid 40 to deliver additional microporous tubes 20 across end regions S1, S2, as illustrated in FIG. 5E.

According to a preferred embodiment, the bioactive matrix comprises a culture medium containing stem cells, and more preferably, proteins (e.g., trypsin) that assist in demyelization and/or steroids that reduce inflammation of the spinal cord and surrounding tissue. As the stem cells mature and differentiate to mimic the environment in which implanted, the cells are expected to penetrate through the walls of the microporous tube to establish interconnections with the surrounding nerve tissue, thereby providing new conductive pathways for both sensory and motor nerves.

Once implanted within the spinal cord, microporous tube 20 is expected to protect the stem cells contained within the bioactive matrix from mechanical stress, and serve as a scaffold for the development and cultivation of the cells. By adding structural support to the spinal cord, microporous tube 20 relieves pressure in the damaged spinal region and retains the severed ends of the spinal cord in alignment.

Figure 6A:
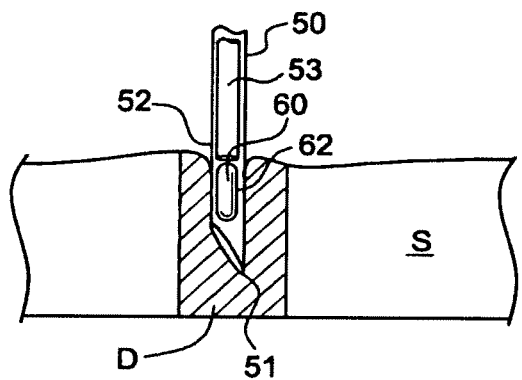
FIGS. 6A-6D are side-sectional views of alternative apparatus and methods of the present invention.

Referring now to FIGS. 6A-6D, alternative methods and apparatus of the present invention for repairing an injured region of spinal cord are described. In FIG. 6A, spinal cord S is shown having injured region D. In accordance with this aspect of the present invention, needle 50 includes tissue-piercing distal end 51, lumen 52 and internal plunger 53. Lumen 52 is sized to accept one or more bioabsorbable microporous tubes pre-loaded with bioactive matrix to form capsules 60.

Capsules 60 comprise a bioactive matrix that includes stem cells and a culture medium that promotes survival of the stem cells. The culture medium also may contain proteins that assist in demyelization and/or steroids that reduce inflammation of the spinal cord and surrounding tissue. As the stem cells mature and differentiate in-situ, they are expected to promote spinal cord nerve cell regeneration of both sensory and motor nerves. In addition, the outer wall of the capsule serves many of the protective and mechanical support functions of the microporous tubes described above, and also may be incorporate anti-rejection drugs and/or agents to promote regeneration of surrounding nerve tissue.

Figure 6B:
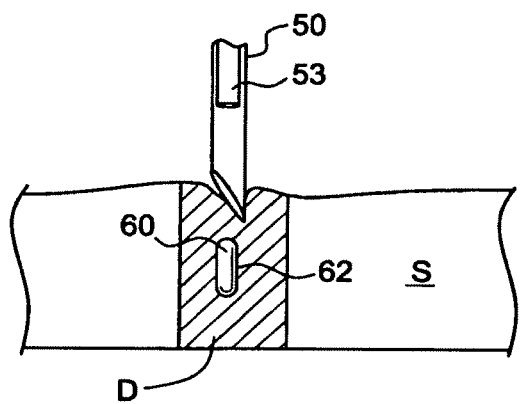

As depicted in FIG. 6A, needle 50 may be employed to directly inject a capsule into injured region D of spinal cord S. First, needle 50 (which is loaded with capsule 60) is inserted into region D. Plunger 53 is then held stationary while needle 50 is retracted proximally, thereby ejecting capsule 60 from lumen 52 of needle 50, as illustrated in FIG. 6B.

Figure 6C:
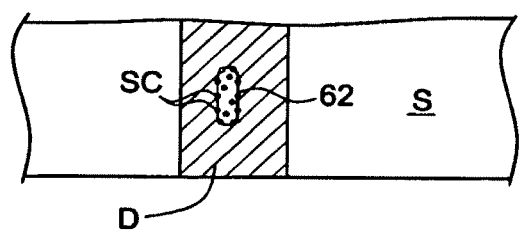
Figure 6D:
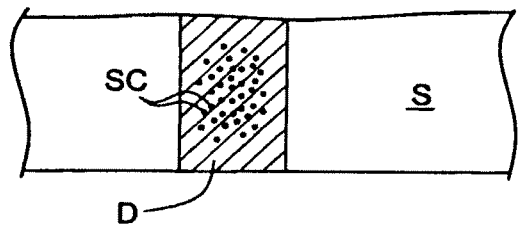

Capsule 60 preferably comprises outer shell 62 that is bioabsorbable, and gradually dissolves once implanted within spinal cord S. As depicted in FIGS. 6C and 6D, as outer shell 62 dissolves, stem cells SC are released into injured spinal cord region D, and migrate throughout the injured region to develop new nerve interconnections that span the injured region.

As will of course be understood, the methods and apparatus of the present invention are applicable not only for repairing nerve cell communication within the spinal cord, but may in addition be used in other nerve cell pathways of the body. For example, the apparatus of the present invention may be employed to re-establish nerve pathways within the brain and other organs of the body.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A method of implanting a microporous tube into a spinal cord, the method comprising:
   performing a vertebral resection to align injured portions of the spinal cord in apposition;
   inserting a microporous tube disposed on an insertion device comprising a needle into the spinal cord at a predetermined location and angle;
   advancing the microporous tube to bridge ends of the injured portions of the spinal cord;
   depositing a bioactive matrix including stem cells capable of differentiating into nerve cells, and a culture medium containing trypsin, within an interior of the microporous tube; and
   removing the needle.

2. The method of claim 1, wherein advancing the microporous tube comprises advancing the microporous tube to a position disposed substantially parallel to a longitudinal axis of the spinal cord.

3. The method of claim 1, further comprising positioning a grid having a plurality of apertures along the spinal cord over the injured prior to inserting the microporous tube and the needle into the spinal cord.

4. The method of claim 1, further comprising guiding insertion of the microporous tube and the needle using a selected one of the plurality of apertures of the grid.

* * * * *